United States Patent
Sang et al.

(10) Patent No.: US 10,407,375 B2
(45) Date of Patent: *Sep. 10, 2019

(54) METHOXYCARBONYLATION WITH FORMIC ACID AS CO SOURCE

(71) Applicant: EVONIK DEGUSSA GMBH, Essen (DE)

(72) Inventors: Rui Sang, Liaocheng (CN); Jie Liu, Solna (SE); Kaiwu Dong, Bo Zhou (CN); Ralf Jackstell, Rostock (DE); Matthias Beller, Ostseebad Nienhagen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,621

(22) Filed: Jul. 24, 2018

(65) Prior Publication Data

US 2019/0047935 A1 Feb. 14, 2019

(30) Foreign Application Priority Data

Aug. 8, 2017 (EP) .................................... 17185346

(51) Int. Cl.
| | | |
|---|---|---|
| *C07C 67/04* | (2006.01) | |
| *B01J 31/24* | (2006.01) | |
| *C07C 67/38* | (2006.01) | |
| *C07F 9/50* | (2006.01) | |
| *C07F 9/58* | (2006.01) | |

(52) U.S. Cl.
CPC ........... *C07C 67/04* (2013.01); *B01J 31/2409* (2013.01); *C07C 67/38* (2013.01); *C07F 9/5027* (2013.01); *C07F 9/58* (2013.01); *B01J 2231/321* (2013.01); *B01J 2531/824* (2013.01)

(58) Field of Classification Search
CPC ....... C07C 67/36; C07C 69/24; C07C 69/612; C07C 67/38; C07C 69/02; C07C 67/04; C07C 69/00; C07C 67/62; C07F 15/0066; C07F 9/5045; C07F 9/5027; C07F 9/58; B01J 2531/824; B01J 31/2409; B01J 31/22; B01J 31/24; B01J 2231/321; C01B 32/39; C07D 471/00

See application file for complete search history.

(56) References Cited

U.S. PATENT DOCUMENTS

| | | |
|---|---|---|
| 9,056,829 B2 | 6/2015 | Parton et al. |
| 9,725,398 B2 | 8/2017 | Dong et al. |
| 2011/0137059 A1 | 6/2011 | Eastham et al. |
| 2017/0022137 A1 | 1/2017 | Dong et al. |
| 2017/0022138 A1 | 1/2017 | Dong et al. |
| 2017/0022139 A1 | 1/2017 | Dong et al. |
| 2017/0022234 A1 | 1/2017 | Jennerjahn et al. |
| 2017/0022235 A1 | 1/2017 | Dong et al. |
| 2017/0022236 A1 | 1/2017 | Dong et al. |

FOREIGN PATENT DOCUMENTS

EP 3 121 185 A2 1/2017

OTHER PUBLICATIONS

Dong et al. (Highly active and efficient catalysts for alkoxycarbonylation of alkenes, Nature Communications, DOI: 10.1038/ncomms14117, pp. 1-7, Published Jan. 2017) (Year: 2017).*
U.S. Appl. No. 16/043,657, Rui Sang, et al., filed Jul. 24, 2018.
U.S. Appl. No. 16/043,644, Rui Sang, et al., filed Jul. 24, 2018.
European Search Report for EP17185346, dated Nov. 21, 2017 (6 pgs.) in German Language.
K. Dong, et al. "Palladium-Catalyzed Carbonylation of sec- and tert-Alcohols", Angewandte Chemie International Edition. Apr. 21, 2017, pp. 6203-6207.
T. Morimoto, et al. "Evolution of Carbonylation Catalysis: No Need for Carbon Monoxide", Angewandte Chemie International Edition. Oct. 25, 2004, pp. 5580-5588.
Arderne, C. et al. Branched Selectivity in the Pd-Catalysed Methoxycarbonylation of 1-Alkenes. ChemCatChem. 2016. vol. 8. pp. 1084-1093.
Sang, R., et al. Palladium-Catalyzed Selective Generation of CO from Formic Acid for Carbonylation of Alekenes. Journal of the American Chemical Society. 2018. vol. 140, pp. 5217-5223.

* cited by examiner

*Primary Examiner* — Yevgeny Valenrod
*Assistant Examiner* — Blaine G Doletski
(74) *Attorney, Agent, or Firm* — Smith, Gambrell & Russell, LLP

(57) ABSTRACT

A catalytic process for the methoxycarbonylation of olefins where formic acid is the CO source. The process includes the steps of forming a reaction mixture where methanol and formic acid are added at a volume ratio in the range from 1.55:0.45 to 1.1:09. The methanol-formic acid ratio enhances both the rate of conversion and methyl ester yield ether produced. The catalysts used is a palladium/benzene-base diphosphine ligand complex.

14 Claims, No Drawings

METHOXYCARBONYLATION WITH FORMIC ACID AS CO SOURCE

The invention relates to a process for methoxycarbonylation with formic acid as the CO source.

The methoxycarbonylation of alkenes is a process of increasing importance. In the classical methoxycarbonylation, an olefin is reacted with CO and MeOH in the presence of a catalyst comprising a ligand and a metal:

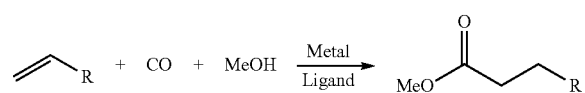

Here, CO is introduced into the reaction vessel as a gas.

It is an object of the invention to provide a process that employs a CO source other than CO gas which is introduced into the reaction vessel. The process should achieve a high yield of methyl ester.

The object is achieved by the process that follows.

Process comprising the process steps of:

a) addition of an olefin;

b) addition of a compound comprising Pd, wherein the Pd is capable of forming a complex;

c) addition of a compound of general formula (I):

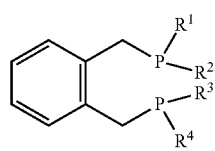

(I)

wherein $R^1$, $R^2$, $R^3$, $R^4$ are each independently selected from: —H, —($C_1$-$C_{12}$)-alkyl, —O—($C_1$-$C_{12}$)-alkyl, —($C_4$-$C_{14}$)-aryl, —O—($C_4$-$C_{14}$)-aryl, cycloalkyl, —($C_1$-$C_{12}$)-heteroalkyl, —O—($C_1$-$C_{12}$)-heteroalkyl, —($C_3$-$C_{14}$)-heteroaryl, —O—($C_3$-$C_{14}$)-heteroaryl, —COO-alkyl, —COO-aryl, —C—O-alkyl, —C—O-aryl, $NH_2$, halogen and the residues are also capable of forming a larger condensed ring;

wherein the recited alkyl groups, aryl groups, cycloalkyl, heteroalkyl groups, heteroaryl groups may be substituted as follows:

—($C_1$-$C_{12}$)-alkyl, —O—($C_1$-$C_{12}$)-alkyl, halogen;

and at least one of the radicals $R^1$, $R^2$, $R^3$, $R^4$ does not represent phenyl;

d) addition of MeOH and HCOOH, wherein the MeOH/HCOOH ratio based on the employed volume is in the range from 1.55:0.45 to 1.1:0.9;

e) heating the reaction mixture to convert the olefin into the methyl ester.

In one variant of e process, no CO gas is supplied to the reaction mixture.

In one variant of the process, HCOOH serves as the only CO source for the reaction.

In one variant of the process, the compound in process step b) is selected from: $Pd(acac)_2$, $PdCl_2$, $Pd(dba)_3*CH_3Cl$ (dba=dibenzylideneacetone), $Pd(OAc)_2$, $Pd(TFA)_2$, $Pd(CH_3CN)Cl_2$.

In one variant of the process, the compound in process step b) is $Pd(OAc)_2$.

In one variant of the process, the process comprises the additional process step f):

f) addition of an acid.

In one variant of the process, the acid is selected from: $H_2SO_4$, $CH_3SO_3H$, $CF_3SO_3H$, PTSA (p-toluenesulfonic acid).

In one variant of the process, the acid is PTSA (p-toluenesulfonic acid).

In one variant of the process, the MeOH/HCOOH ratio based on the employed volume is in the range from 1.5:0.5 to 1.2:0.8.

In one variant of the process, $R^1$, $R^2$, $R^3$, $R^4$ are each independently selected from: —($C_1$-$C_{12}$)-alkyl, —O—($C_1$-$C_{12}$)-alkyl, —($C_4$-$C_{14}$)-aryl, —O—($C_4$-$C_{14}$)-aryl, cycloalkyl, —($C_1$-$C_{12}$)-heteroalkyl, —O—($C_1$-$C_{12}$)-heteroalkyl, —($C_3$-$C_{14}$)-heteroaryl, —O—($C_3$-$C_{14}$)-heteroaryl, —COO-alkyl, —COO-aryl, —C—O-alkyl, —C—O-aryl, $NH_2$, halogen and the residues are also capable of forming a larger condensed ring; wherein the recited alkyl groups, aryl groups, cycloalkyl, heteroalkyl groups, heteroaryl groups may be substituted as follows:

—($C_1$-$C_{12}$)-alkyl, —O—($C_1$-$C_{12}$)-alkyl, halogen;

and at least one of the radicals $R^1$, $R^2$, $R^3$, $R^4$ does not represent phenyl.

In one variant of the process, $R^1$, $R^2$, $R^3$, $R^4$ are each independently selected from: —($C_1$-$C_{12}$)-alkyl, —($C_4$-$C_{14}$)-aryl, cycloalkyl, —($C_1$-$C_{12}$)-heteroalkyl, —($C_3$-$C_{14}$)-heteroaryl, halogen and the residues are also capable of forming a larger condensed ring;

wherein the recited alkyl groups, aryl groups, cycloalkyl, heteroalkyl groups, heteroaryl groups may be substituted as follows:

—($C_1$-$C_{12}$)-alkyl, —O—($C_1$-$C_{12}$)-alkyl, halogen;

and at least one of the radicals $R^1$, $R^2$, $R^3$, $R^4$ does not represent phenyl.

In one variant of the process, $R^1$, $R^2$, $R^3$, $R^4$ are each independently selected from: —($C_1$-$C_{12}$)-alkyl, cycloalkyl, —($C_3$-$C_{14}$)-heteroaryl and the residues are also capable of forming a larger condensed ring;

wherein the recited alkyl groups, cycloalkyl, heteroaryl groups may be substituted as follows:

—($C_1$-$C_{12}$)-alkyl, —O—($C_1$-$C_{12}$)-alkyl, halogen, and at least one of the radicals $R^1$, $R^2$, $R^3$, $R^4$ does not represent phenyl.

In one variant of the process, $R^1$, $R^4$ are each independently selected from: —($C_1$-$C_{12}$)-alkyl, cycloalkyl and the residues are also capable of forming a larger condensed ring;

wherein the recited alkyl groups, cycloalkyl may be substituted as follows:

—($C_1$-$C_{12}$)-alkyl, —O—($C_1$-$C_{12}$)-alkyl, halogen.

In one variant of the process, $R^2$, $R^3$ each independently represent —($C_3$-$C_{14}$)-heteroaryl, wherein the recited heteroaryl groups may be substituted as follows: —($C_1$-$C_{12}$)-alkyl, —O—($C_1$-$C_{12}$)-alkyl, halogen.

In one variant of the process, the compound of general formula (I) has the structure (2):

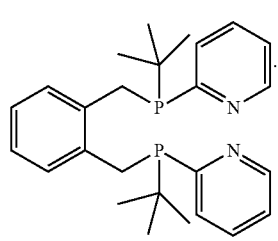

(2)

In one variant of the process, the compound of general formula (I) has the structure (3):

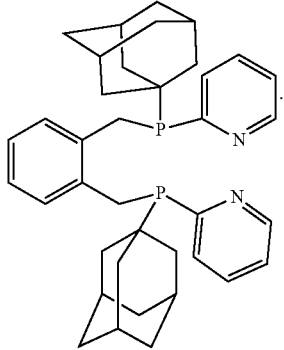

(3)

In addition to the process, a compound as such is also claimed.

Comoound having the structure (3):

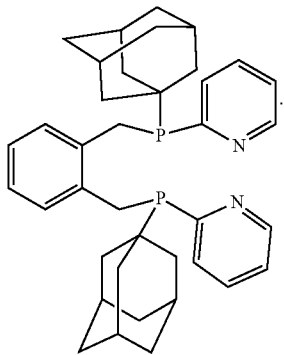

(3)

The invention is more particularly elucidated hereinbelow with reference to working examples.

A) Pd-Catalyzed Methoxycarbonylation of Tetramethylethylene 1a with HCOOH: Effect of MeOH to HCOOH Ratio

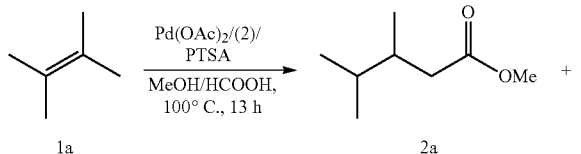

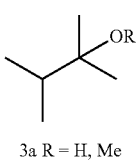

3a R = H, Me

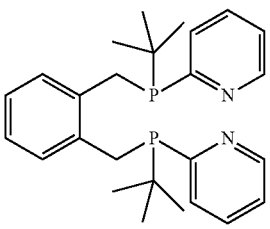

(2)

Added to a sealed 35 ml tube were [Pd(OAc)$_2$] (1.12 mg, 0.25 mol %), (2) (8.72 mg, 1.0 mol %), p-toluenesulfonic acid (PTSA.H$_2$O) (15.2 mg, 4 mol %) and an oven-dried stirrer bar. The tube was placed together with the lid into a long Schlenk tube having a large opening. The Schlenk tube is evacuated three times and refilled with argon. Under an argon atmosphere 1a (2 mmol), MeOH (X ml) and HCOOH (Y ml) (X ml+Y ml=2 ml) were injected into the 35 ml tube using a syringe. The 35 ml tube was then sealed with the lid. The reaction was carried out at 100° C. over 13 h. After the reaction had ended, the tube was allowed to reach room temperature without additional cooling and carefully decompressed. Isooctane (100 µl) was then injected as internal standard. Conversion was measured by GC analysis.

The results are summarized in table 1 which follows

TABLE 1

| MeOH/HCOOH (altogether 2 ml) | Conversion % | Yield of 2a % | Yield of 3a % |
| --- | --- | --- | --- |
| 1.8/0.2 | 63 | 36 | 24 |
| 1.6/0.4 | 70 | 49 | 19 |
| 1.5/0.5 | 76 | 62 | 13 |
| 1.4/0.6 | 76 | 61 | 13 |
| 1.2/0.8 | 78 | 66 | 10 |
| 1.0/1.0 | 74 | 48 | 10 |

B) Pd-Catalyzed Methoxycarbonylation of Tetramethylethylene 1a with HCOOH: Effect of the Ligand

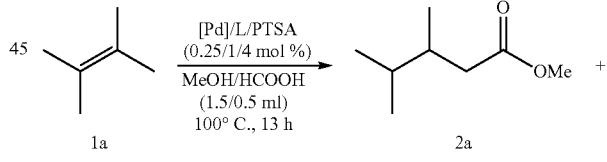

3a R = H, Me

Added to a sealed 35 ml tube under an argon atmosphere were [Pd(OAc)$_2$] (1.12 mg, 0.25 mol %), ligand (1 mol %), p-toluenesulfonic acid (PTSA.H$_2$O) (15.2 mg, 4 mol %) and an oven-dried stirrer rod. The tube was placed together with the lid into a long Schlenk tube having a large opening. The Schlenk tube was evacuated three times and refilled with argon. 1a (2 mmol), HCOOH (0.5 ml) and MeOH (1.5 ml) were injected into the 35 ml tube using a syringe. The 35 ml tube was then sealed with the lid. The reaction was carried out at 100° C. over 13 h. After the reaction had ended, the tube was allowed to reach room temperature without additional cooling (if very cold water used, tube can burst) and carefully decompressed. Isooctane (100 μl) was then injected as internal standard. Conversion was measured by GC analysis.

The results are summarized in table 2 which follows:

TABLE 2

| Ligand (L) | Conversion % | Yield of 2a % | Yield of 3a % |
|---|---|---|---|
| 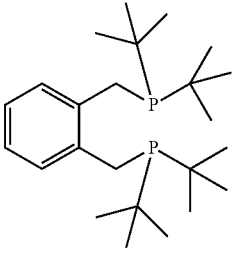 (1) | 60 | 32 | 22 |
| 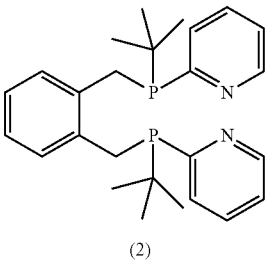 [SMILES: CC(C)(C)P(Cc1ccccc1CP(c1ccccn1)C(C)(C)C)c1ccccn1] (2) | 76 | 62 | 13 |
| 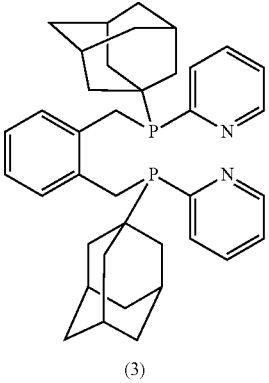 [SMILES: c1ccc(P(Cc2ccccc2CP(c2ccccn2)C23CC4CC(CC(C4)C2)C3)C23CC4CC(CC(C4)C2)C3)nc1] (3) | 83 | 67 | 13 |
| 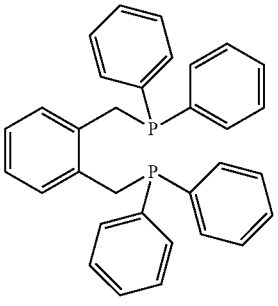 (4) | 40 | 0 | 35 |

TABLE 2-continued

| Ligand (L) | Conversion % | Yield of 2a % | Yield of 3a % |
|---|---|---|---|
| 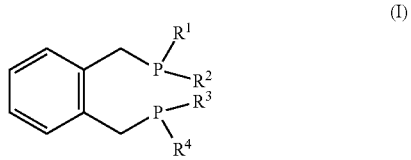 (5) | 38 | 0 | 31 |

As is shown by the experiments described above, the object is achieved by a process according to the invention.

The invention claimed is:

1. A process for the methoxycarbonylation of olefins to form methyl esters comprising the process steps of:
    a) adding an olefin to form a reaction mixture;
    b) introducing to the mixture a compound comprising Pd, wherein the Pd is capable of forming a complex;
    c) introducing to the mixture a compound of general formula (I):

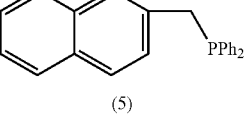

(I)

wherein $R^1$, $R^2$, $R^3$, $R^4$ are each independently selected from: —H, —$(C_1$-$C_{12})$-alkyl, —O—$(C_1$-$C_{12})$-alkyl, —$(C_4$-$C_{14})$-aryl, —O—$(C_4$-$C_{14})$-aryl, cycloalkyl, —$(C_1$-$C_{12})$-heteroalkyl, —O—$(C_1$-$C_{12})$-heteroalkyl, —$(C_3$-$C_{14})$-heteroaryl, —O—$(C_3$-$C_{14})$-heteroaryl, —COO-alkyl, —COO-aryl, —C—O-alkyl, —C—O-aryl, $NH_2$, and halogen;

wherein the recited alkyl groups, aryl groups, cycloalkyl, heteroalkyl groups, heteroaryl groups may be substituted as follows:

—$(C_1$-$C_{12})$-alkyl, —O—$(C_1$-$C_{12})$-alkyl, halogen;

and at least one of the radicals $R^1$, $R^2$, $R^3$, $R^4$ does not represent phenyl;

d) introducing to the mixture MeOH and HCOOH, wherein the MeOH/HCOOH ratio based on the employed volume is in the range from 1.55:0.45 to 1.1:0.9;
    e) heating the reaction mixture to convert the olefin into the methyl ester.

2. The process according to claim 1, wherein no CO gas is supplied to the reaction mixture.

3. The process according to claim 1, wherein HCOOH serves as the only CO source for the reaction.

4. The process according to claim 1, wherein the compound in process step b) is selected from: $Pd(acac)_2$, $PdCl_2$, $Pd(dba)_3*CH_3Cl$ (dba=dibenzylideneacetone), $Pd(OAc)_2$, $Pd(TFA)_2$, $Pd(CH_3CN)Cl_2$.

5. The process according to claim 1, wherein the process comprises additional process step f):
    f) addition of an acid.

6. The process according to claim 5,
wherein the acid is selected from: $H_2SO_4$, $CH_3SO_3H$, $CF_3SO_3H$, PTSA.

7. The process according to claim 1,
wherein the MeOH/HCOOH ratio based on the employed volume is in the range from 1.5:0.5 to 1.2:0.8.

8. The process according to claim 1,
wherein $R^1$, $R^2$, $R^3$, $R^4$ are each independently selected from: —$(C_1-C_{12})$-alkyl, —$(C_4-C_{14})$-aryl, —O—$(C_4-C_{14})$-aryl, cycloalkyl, —$(C_1-C_{12})$-heteroalkyl, —O—$(C_1-C_{12})$-heteroalkyl, —$(C_3-C_{14})$-heteroaryl, —O—$(C_3-C_{14})$-heteroaryl, —COO-alkyl, —COO-aryl, —C—O-alkyl, —C—O-aryl, $NH_2$, halogen and the residues are also capable of forming a larger condensed ring;
wherein the recited alkyl groups, aryl groups, cycloalkyl, heteroalkyl groups, heteroaryl groups may be substituted as follows:
$(C_1-C_{12})$-alkyl, —O—$(C_1-C_{12})$-alkyl, halogen;
and at least one of the radicals $R^1$, $R^2$, $R^3$, $R^4$ does not represent phenyl.

9. The process according to claim 1,
wherein $R^1$, $R^2$, $R^3$, $R^4$ are each independently selected from: —$(C_1-C_{12})$-alkyl, —$(C_4-C_{14})$-aryl, cycloalkyl, —$(C_1-C_{12})$-heteroalkyl, —$(C_3-C_{14})$-heteroaryl, halogen and the residues are also capable of forming a larger condensed ring;
wherein the recited alkyl groups, aryl groups, cycloalkyl, heteroalkyl groups, heteroaryl groups may be substituted as follows:
—$(C_1-C_{12})$-alkyl, —O—$(C_1-C_{12})$-alkyl, halogen;
and at least one of the radicals $R^1$, $R^2$, $R^3$, $R^4$ does not represent phenyl.

10. The process according to claim 1,
wherein $R^1$, $R^2$, $R^3$, $R^4$ are each independently selected from: —$(C_1-C_{12})$-alkyl, cycloalkyl, —$(C_3-C_{14})$-heteroaryl and the residues are also capable of forming a larger condensed ring;
wherein the recited alkyl groups, cycloalkyl, heteroaryl groups may be substituted as follows:
—$(C_1-C_{12})$-alkyl, —O—$(C_1-C_{12})$-alkyl, halogen,
and at least one of the radicals $R^1$, $R^2$, $R^3$, $R^4$ does not represent phenyl.

11. The process according to claim 1,
wherein $R^1$, $R^4$ are each independently selected from: —$(C_1-C_{12})$-alkyl, cycloalkyl and the residues are also capable of forming a larger condensed ring;
wherein the recited alkyl groups, cycloalkyl may be substituted as follows:
—$(C_1-C_{12})$-alkyl, —O—$(C_1-C_{12})$-alkyl, halogen.

12. The process according to claim 1,
wherein $R^2$, $R^3$ each independently represent —$(C_3-C_{14})$-heteroaryl,
wherein the recited heteroaryl groups may be substituted as follows:
—$(C_1-C_{12})$-alkyl, —O—$(C_1-C_{12})$-alkyl, halogen.

13. The process according to claim 1,
wherein the compound of general formula (I) has the structure (2):

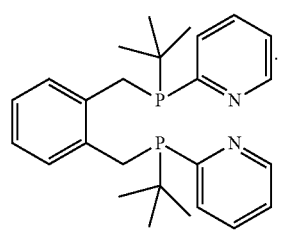

(2)

14. The process according to claim 1,
wherein the compound of general formula (I) has the structure (3):

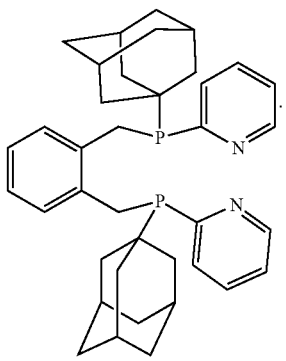

(3)

* * * * *